(12) United States Patent
Bloomberg et al.

(10) Patent No.: US 10,591,419 B2
(45) Date of Patent: Mar. 17, 2020

(54) PH COLOUR INDICATOR FOR USE WITH AGRICULTURAL COMPOUNDS

(71) Applicant: NutriAg Ltd., Toronto (CA)

(72) Inventors: Martin David Bloomberg, Toronto (CA); Mark Stewart Houston-McMillan, Toronto (CA)

(73) Assignee: Nutriag Ltd., Toronto (CA)

( * ) Notice: Subject to any disclaimer, the term of this patent is extended or adjusted under 35 U.S.C. 154(b) by 0 days.

(21) Appl. No.: 16/180,680

(22) Filed: Nov. 5, 2018

(65) Prior Publication Data
US 2019/0072494 A1    Mar. 7, 2019

Related U.S. Application Data

(60) Division of application No. 10/570,048, filed as application No. PCT/CA2004/001555 on Aug. 24, 2004, now Pat. No. 10,145,803, which is a continuation of application No. 10/646,928, filed on Aug. 25, 2003, now abandoned.

(51) Int. Cl.
| | |
|---|---|
| G01N 21/80 | (2006.01) |
| A01N 65/00 | (2009.01) |
| C05G 3/00 | (2020.01) |
| A01N 65/03 | (2009.01) |
| A01N 65/08 | (2009.01) |

(52) U.S. Cl.
CPC .............. *G01N 21/80* (2013.01); *A01N 65/00* (2013.01); *A01N 65/03* (2013.01); *A01N 65/08* (2013.01); *C05G 3/00* (2013.01)

(58) Field of Classification Search
CPC ........ G01N 21/80; A01N 65/03; A01N 65/08; A01N 65/00; C05G 3/00
See application file for complete search history.

(56) References Cited

U.S. PATENT DOCUMENTS

| | | | |
|---|---|---|---|
| 4,939,086 | A | 7/1990 | Vunsh et al. |
| 5,278,132 | A | 1/1994 | Fisher et al. |
| 6,036,666 | A | 3/2000 | Peiler et al. |
| 6,132,791 | A | 10/2000 | Fox |
| 6,589,761 | B1 | 7/2003 | Freadman et al. |
| 2001/0012636 | A1 | 8/2001 | Azar et al. |
| 2004/0121050 | A1 | 6/2004 | Thurman et al. |
| 2005/0233919 | A1 | 10/2005 | Rich |

FOREIGN PATENT DOCUMENTS

| | | |
|---|---|---|
| EP | 760482 A2 | 5/1997 |
| WO | 9925189 A1 | 5/1999 |
| WO | 2004025254 A2 | 3/2004 |

OTHER PUBLICATIONS

Lopes Terci et al (Quimica Nova, vol. 4, No. 4, Jul. 2002 (Year: 2002).*

Daniela Brotto Lopes Terci et al, "Indicadores Naturals de pH: usar papel ou solucao?", Quimica Nova, vol. 25, No. 4, Jul. 2002.
Steven S. Zumdahl, Chimie (chimie des solutions); textbook; Ed. Centre Educatif et Culturel inc., Montreal, 381 pages, 1998, p. 218.
Bakowska-Barczak et al., "Acylated Anthocyanins as Stable, Natural Food Colorants—A Review", Pol. J. Food Nurtr. Sci., 2005, vol. 14/55, No. 2, pp. 107-116.
Charron et al., Effect of Dose Size on Bioavailability of Aclated and Nonacylated Anthocyanins from Red Cabbage (*Brassica oleracea* L. Var. *Capitata*), Journal of Agricultural and Food Chemistry, 2007, vol. 55, pp. 5354-5362.
Dao et al, "Improved Method for the Stablization of Anthocyanidins", J. Agric. Food Chem., 1998, vol. 46, pp. 3564-3569.
Davies et al., "Copigmentation of Simple and Acylaated Anthocyanins with Colorless Phenolic Compounds", J. Agric. Food Chem., 1993, vol. 41, pp. 716-720.
Dyrby et al., "Light and Heat Sensitivity of Red Cabbage Extract in Soft Drink Model Systems", Food Chemistry, 2001. vol. 72, pp. 434-437.
Huang et al., "Identification of Anthocyanins in Muscadinegrapes with HPLC-ESI-MS", LWT-Food Science and Technology, 2009, vol. 42, pp. 819-824.
Inert Ingredients Permitted for Use in Nonfood Use Pesticide Products, Untied States Environmental Protection Agency; last updated Apr. 2011, 77 pages.
Kong et al., "Analysis and Biological Activities of Anthocyanins", Phytochemistry, 2003, vol. 63, pp. 923-933.
Malien-Aubert et al., "Color Stability of Commercial Anthocyanin Based Extracts in Relation to the Phenolic Composition. Protective Effects by Intra and Intermolecular Copigmentation", J. Agric. Food Chem., 2001, vol. 49, pp. 170-176.
Pinheiro et al., "Total Phenolics and Total Anthocyanins Found in Grape form Benitaka Cultivar", Journal of Food Technology, 2009, vol. 7(3), pp. 78-83.
Puntener et al., "European Ban on Certain Azo Dyes", www.tfl.com, Jan. 5, 2004, pp. 1-6.
Revilla et al., "Comparison of Several Procedures Used for the Extraction of Anthocyanins from Red Grapes", J. Agric. Food Chem., 1998, vol. 46, pp. 4592-4597.
Science is Fun, "Exploring Acids and Bases", http://scifun.chem.wisc.edu/HOMEEXPTS/ACIDBASE.html, Nov. 4, 2013, 3 pages.
Chemistry Land, "Part 2: Preparing Red Cabbage Extract", http://www.chemistryland.com/CHM107Lab/Lab1/Lab1PreparingCabbageExtract.htm, Jun. 21, 2010.
Chigurupati N. et al., Evaluation of Red Cabbage Dye as a Potential Natural Color for Pharmaceutical Use, International Journal of Pharmaceutics, 2002, vol. 241(2), pp. 293-299.

\* cited by examiner

*Primary Examiner* — Dennis White
(74) *Attorney, Agent, or Firm* — Bereskin & Parr LLP/S.E.N.C.R.L., S.R.L.; Patricia Folkins

(57) ABSTRACT

This invention discloses a new class of pH indicators suitable for use in agricultural compounds. The class comprises naturally occurring substances which are extracts from grape skins, cabbage and lecithin. Safety concerns are now causing regulatory bodies to prohibit use of chemical pH indicators in compounds which are used for crops and animals. The naturally occurring compounds of this invention satisfy these concerns of the regulators and function as well as chemical indicators of the prior art.

5 Claims, No Drawings

PH COLOUR INDICATOR FOR USE WITH AGRICULTURAL COMPOUNDS

The present application is a division of co-pending U.S. patent application Ser. No. 10/570,048 filed on Dec. 12, 2006, which is a national stage of International Application No. PCT/CA2004/01555, filed on Aug. 24, 2004, which claims the benefit of priority from U.S. patent application Ser. No. 10/646,928 filed on Aug. 25, 2003, the contents of each of which are incorporated herein by reference.

This invention relates to agricultural compounds and more particularly to an improved agricultural compound which uses a natural occurring pH indicator rather than a chemical pH indicator.

DESCRIPTION OF THE PRIOR ART

U.S. Pat. No. 5,278,132 granted to Gouws & Scheepers (Proprietary) Limited discloses a concentrate for dilution with water useful in the production of agricultural compounds for application to crops, soil or animals. The concentrate is added to the agricultural compound and then diluted with water until the desired pH is reached. This desired level of pH is controlled by the agricultural compound.

The patent discloses several chemicals which are used to determine the level of pH. These compounds include methyl red, resorcin blue, 2,5-dinitrophenol and chlorophenol red. These pH indicators change colour when the pH is changed and accordingly, provide a visual indicator as to when the desired pH is reached.

However, regulatory authorities throughout the world are now discouraging the use of non-natural ingredients especially when the agricultural compounds are used on crops and for treatment of animals. As a result, the chemical pH indicators currently in use are being rejected by regulatory authorities.

The Food and Drug Agency of the United States government sets out specifications of products which are approved for such use. These specifications are contained in, inter alia, Federal regulations, Title 21, Part 73.170. It is noted that methyl red is not listed and is therefore not an approved product.

Similarly, the European Economic Commission has also issued directives as contained in the EEC Additives No. E163 (Commission directive 95/45/EC as amended) which lists approved products for such use.

BRIEF DESCRIPTION OF THE INVENTION

Accordingly, the present invention provides an improvement wherein a completely naturally occurring product is used as the pH indicator.

To this end, in one of its aspects, the invention provides a naturally occurring pH indicator for use in a concentrate for preparing an agricultural compound which comprises an extract from grapes, cabbage or lichen.

In another of its aspects, the invention provides a concentrate comprising a mixture of a pH modifying agent and a naturally occurring pH indicator for colouring water, which concentrate can be diluted with water and added to an agricultural chemical for application to crops, soil or animals, the agricultural chemical having an activity that varies with the pH of the water and having an acceptable agricultural activity at a pH within the range of 4-6, wherein the proportions of pH modifying agent and pH indicator in the concentrate are such that when the concentrate is diluted with water and the pH of the water is modified by the pH modifying agent, the pH indicator indicates visually when the pH of the water is in the range of from about 4 to about 6.

DESCRIPTION OF THE PREFERRED EMBODIMENT

The inventors have discovered that several naturally occurring products may be used as the colour/pH indicator in the concentrate as disclosed in U.S. Pat. No. 5,278,132. These naturally occurring compounds produce the same colour changes as do the chemical compounds but are acceptable to regulatory authorities throughout the world. These compounds exhibit no untoward activity to plants or animals.

The pH indictor of the present invention is selected from the group consisting of extracts from grape skins, cabbage or lichen. Extracts of grape skins are preferred because the required concentration is less but extracts of cabbage and lichen are also acceptable although they do require a higher concentration.

It is desired that the pH indicator change colour at a pH from about 4 to about 6. It is also desired that the indicator not have any deleterious effects on the crops or animals and it is for this reason that the naturally occurring products of the invention are so useful.

The grapes are first processed to remove the juice from the grapes to produce grape juice or wine and then the skin of the grape is removed. The grape skin extract is a purplish-red liquid which is prepared by the aqueous extraction of the fresh deseeded marc remaining after the grapes have been pressed. The extract contains anthocyanins, tartaric acid, tannins, sugars and minerals but not in the same proportions as in the grape juice. During the steeping process, sulphur dioxide is added and most of the extracted sugars are fermented to alcohol. The extract is then concentrated by vacuum evaporation during which almost all of the alcohol is removed. A small amount of sulphur dioxide may be present.

The extract shows a blue colour at a pH greater than 5 and a red colour at a pH lower than 5.

This extract was tested in the formulations disclosed in U.S. Pat. No. 5,278,132 and excellent results were obtained. However, it was found that much higher concentrations were required to show the visual colour change. Concentrations in the range of 10 to 25% were necessary to show the colour changes.

The experiments were repeated using cabbage extract and lichen extract. These worked although higher concentrations were necessary. Thus, while they clearly fall within the scope of this invention, the preferred product is grape extract.

An example of the concentrate (acid adjuvant) suitable for pH reduction, control and buffering in aqueous agricultural compositions for application to plants or soil an alkali sensitive agricultural chemicals subject to degradation in alkaline environments was formulated with the following composition:

| | |
|---|---|
| Nonyl phenoxy polyoxyethylene glycol | 10.4 |
| Monoortho-phosphoric esters | 43.6 |
| Diorthophosphoric esters | 2.9 |
| Isopropyl alcohol | 15.6 |
| Water | 17.5 |
| Grape skin extract | 10.0 |

All percentages are expressed in mass/mass.

A second example of the concentrate (acid adjuvant) suitable for pH reduction, control and buffering in aqueous agricultural compositions for application to plants or soil an alkali sensitive agricultural chemicals subject to degradation in alkaline environments was formulated with the following composition:

| | |
|---|---|
| Nonyl phenoxy polyoxyethylene glycol | 10.4 |
| Monoortho-phosphoric esters | 43.6 |
| Diorthophosphoric esters | 2.9 |
| Isopropyl alcohol | 15.6 |
| Cabbage Extract | 27.5 |

All percentages are expressed in mass/mass.

A third example of the concentrate (acid adjuvant) suitable for pH reduction, control and buffering in aqueous agricultural compositions for application to plants or soil an alkali sensitive agricultural chemicals subject to degradation in alkaline environments was formulated with the following composition:

| | |
|---|---|
| Nonyl phenoxy polyoxyethylene glycol | 10.4 |
| Monoortho-phosphoric esters | 43.6 |
| Diorthophosphoric esters | 2.9 |
| Isopropyl alcohol | 15.6 |
| Lichen extract | 27.5 |

All percentages are expressed in mass/mass.

Accordingly, the use of a naturally occurring pH indicator represents a significant advance.

Although the invention describes and illustrates a preferred embodiment of the invention, kit is understood that it is no so restricted and includes in its scope, variations thereof.

We claim:

1. A liquid concentrate comprising a mixture of:
an acidic pH modifying agent; and
a naturally occurring pH indicator for coloring water, said naturally occurring pH indicator consisting of an extract of cabbage,
wherein the proportions of the pH modifying agent and the pH indicator in the concentrate are such that when the concentrate is diluted with water and the pH of the water is modified by the pH modifying agent, the pH indicator indicates visually by a color change when the pH of the water is in the range of from about 4 to about 6.

2. The concentration of claim 1, wherein the cabbage extract is present in an amount of 27.5% by weight of the concentrate.

3. The concentrate of claim 1, wherein the concentrate comprises:
27.5% by weight of the concentrate of the extract of cabbage;
10.4% by weight of the concentrate of nonyl phenoxy polyoxyethylene glycol;
43.6% by weight of the concentrate of monoortho-phosphoric esters;
2.9% by weight of the concentrate of diorthophosphoric esters; and
15.6% by weight of the concentrate of isopropyl alcohol.

4. A kit comprising the liquid concentrate of claim 1 and instructions for diluting with water and combining with an agricultural chemical for application to crops, soil or animals.

5. The kit of claim 4, wherein the agricultural chemical has an activity that varies with the pH of the water and has an acceptable agricultural activity at a pH within the range of 4-6.

* * * * *